US012599690B2

(12) United States Patent
Malik et al.

(10) Patent No.: US 12,599,690 B2
(45) Date of Patent: Apr. 14, 2026

(54) MEDICAL OR DENTAL CASSETTE

(71) Applicants: Hassan Malik, Sialkot (PK); Haseeb Sajid, West New York, NJ (US)

(72) Inventors: Hassan Malik, Sialkot (PK); Haseeb Sajid, West New York, NJ (US)

( * ) Notice: Subject to any disclaimer, the term of this patent is extended or adjusted under 35 U.S.C. 154(b) by 440 days.

(21) Appl. No.: 18/140,763

(22) Filed: Apr. 28, 2023

(65) Prior Publication Data

US 2024/0358875 A1     Oct. 31, 2024

(51) Int. Cl.
*A61L 2/26*       (2006.01)
*A61B 50/33*      (2016.01)

(52) U.S. Cl.
CPC ............... *A61L 2/26* (2013.01); *A61B 50/33* (2016.02); *A61L 2202/24* (2013.01)

(58) Field of Classification Search
CPC ...... A61B 2050/0069; A61B 2050/007; A61B 2050/0074; A61B 2050/008; A61B 2050/0081; A61B 50/30; A61L 2/26; A61L 2202/24
USPC .............. 206/439, 63.5, 561, 369, 389, 1.5; 24/287, 314, 307, 322.1; 220/281; 70/214, 220, DIG. 20; 292/DIG. 37
See application file for complete search history.

(56) References Cited

U.S. PATENT DOCUMENTS

| | | | | |
|---|---|---|---|---|
| 4,541,992 A | * | 9/1985 | Jerge | A61B 50/31 |
| | | | | 422/310 |
| 4,959,199 A | * | 9/1990 | Brewer | A61C 19/00 |
| | | | | 206/439 |
| 5,279,800 A | * | 1/1994 | Berry, Jr. | A61L 2/26 |
| | | | | 206/370 |
| 5,281,400 A | * | 1/1994 | Berry, Jr. | A61L 2/26 |
| | | | | 422/561 |
| 5,294,413 A | * | 3/1994 | Riihimaki | A61L 2/06 |
| | | | | 206/370 |
| 5,346,677 A | * | 9/1994 | Risk | A61L 2/26 |
| | | | | 248/500 |
| 5,451,379 A | * | 9/1995 | Bowlin, Jr. | A61L 2/20 |
| | | | | 292/DIG. 31 |
| 5,490,975 A | * | 2/1996 | Dane | A61L 2/26 |
| | | | | 206/439 |
| 5,505,916 A | * | 4/1996 | Berry, Jr. | A61L 2/26 |
| | | | | 206/483 |
| 5,573,741 A | * | 11/1996 | Riley | A61L 2/07 |
| | | | | 206/439 |
| 5,725,097 A | * | 3/1998 | Bettenhausen | A61L 2/26 |
| | | | | 292/210 |
| 6,012,577 A | * | 1/2000 | Lewis | A61L 2/26 |
| | | | | 206/439 |
| 6,048,503 A | * | 4/2000 | Riley | A61L 2/26 |
| | | | | 422/26 |
| 6,116,452 A | * | 9/2000 | Hamel | B65D 45/20 |
| | | | | 220/345.2 |

(Continued)

FOREIGN PATENT DOCUMENTS

WO     WO-2008078169 A2 *   7/2008  .......... E05B 53/003

*Primary Examiner* — Rafael A Ortiz
(74) *Attorney, Agent, or Firm* — OSTROLENK FABER LLP

(57)             ABSTRACT

A cassette that includes at least one tray defined by a plurality of walls extending from a panel to receive at least one dental instrument in a reception space defined by the walls, and a locking mechanism, or at least one lockable lock bar, or one part of a coupling mechanism, located in the reception space.

15 Claims, 13 Drawing Sheets

(56)  References Cited

U.S. PATENT DOCUMENTS

| | | | |
|---|---|---|---|
| 6,193,932 B1 * | 2/2001 | Wu | A61L 2/07 |
| | | | 206/439 |
| 7,044,509 B2 * | 5/2006 | Radel | E05C 1/04 |
| | | | 292/147 |
| 8,267,246 B2 * | 9/2012 | Bettenhausen | A61B 50/30 |
| | | | 206/439 |
| 2004/0144670 A1 * | 7/2004 | Riley | A61B 50/30 |
| | | | 206/439 |
| 2006/0213794 A1 * | 9/2006 | Foreman | A61L 2/26 |
| | | | 206/439 |
| 2007/0104609 A1 * | 5/2007 | Powell | A61L 2/26 |
| | | | 206/370 |
| 2008/0229792 A1 * | 9/2008 | Maple | G09F 3/0358 |
| | | | 292/307 R |
| 2015/0203265 A1 * | 7/2015 | Hill | E05B 19/0005 |
| | | | 70/31 |
| 2019/0255207 A1 * | 8/2019 | Oko | F16B 2/22 |

* cited by examiner

MEDICAL OR DENTAL CASSETTE

FIELD OF THE INVENTION

The present invention relates to a medical or dental cassette (hereafter "cassette") for housing and sterilization of medical or dental instruments.

BACKGROUND OF THE INVENTION

Cassettes for housing and sterilization of dental instruments are known.

A typical known cassette includes two trays rotatably coupled to one another by hinges.

The trays may be kept in a closed state with a latch type device, for example.

A typical known cassette may have racks installed in the trays for receiving dental instruments, and a push bar, that is not lockable in place, to hold down the dental instruments.

SUMMARY OF THE INVENTION

It is an object of the present invention to provide a cassette with improved features.

A cassette according to the present invention includes a tray that comprises a plurality of walls extending from a panel to define a reception space for receiving at least one dental instrument; and a locking mechanism, or at least one lockable lock bar, or one part of a coupling mechanism, in the reception space.

A cassette according to the present invention may have two trays that are locked by a locking mechanism.

A cassette according to the present invention may have two trays, a lockable lock bar associated with each tray, and a respective locking mechanism for each lockable lock bar.

A cassette according to the present invention may have two trays with a coupling mechanism that rotatably couples the two trays for rotation relative to one another, the coupling mechanism having one part associated with one tray, and another part associated with the other tray, the one part and the another part of the coupling mechanism being disengageably engageable to permit selective coupling and decoupling of the trays.

A cassette according to the present invention may include any one of, all of, or any combination of a locking mechanism, a lockable lock bar, and a coupling mechanism.

The locking mechanism may include a lock housing, a lock pin, and a resilient body coupled to the lock pin to urge the lock pin toward a lock position.

The lock pin is configured to lock a lock catch that may be at one end of a lock bar or attached to another tray.

The lock pin may have a first section and a second section, the first section of the lock pin having a diameter smaller than the second section of the lock pin.

The lock catch may be a body (for example, a flat body in the shape of a tab) having a cutout that has a first section wider than the first section of the lock pin but narrower than the second section of the lock pin. The cutout may have a second section that is wide enough to receive the second section of the lock pin. In the locked state, the second section of the lock pin is received in the second section of the cutout, and in the released state, the second section is outside the second section of the cutout to permit the first section of the lock pin to pass through the first section of the cutout.

The locking mechanism may further include a push button connected to the lock pin, wherein the application of a force sufficient to compress the resilient body moves the lock pin from the locked state to the released state.

The cutout in the lock catch may be configured so that surfaces adjacent the first section of the cutout engage the second section of the lock pin as the first section of the lock pin is inserted into the first section of the cutout to compress the resilient body. When the surfaces adjacent the first section of the cutout no longer engage the second section of the lock pin, the compressed resilient body decompresses and urges the second section of the lock pin to enter the second section of the cutout thereby coupling the lock pin and the lock catch to realize the locked state.

The locking mechanism may further have at least one push pin that abuts the lock catch in the locked state, and another resilient body connected to the push pin that is compressed in the locked state, whereby the lock catch is pushed away by the push pin in the released state as the another resilient body decompresses.

A cassette according to the present invention may include another tray rotatably coupled to the tray with the locking mechanism residing at a front wall of the tray in the reception space, and the lock catch residing at the front wall of the another tray.

The lock bar may be an elongated body having a lock catch at one end thereof, and a tongue at another end thereof, the tongue being receivable in a slot defined in one wall of the tray, and the lock catch is lockable by a locking mechanism located in the reception space and at another wall of the tray opposite the one wall.

The lock bar may include a compliant body coupled to the lock bar.

The compliant body may have a base portion, and two wings extending from the base portion.

The lock bar may include a base and two wing portions extending from the base of the lock bar to define a channel with the base portion of the compliant body received in the channel.

The wing portions of the lock bar may be tilted toward one another. Part of the base portion of the compliant body may be located in a gap between free edges of the wing portions of the lock bar. The base portion of the compliant body may have a cross-section that widens in a direction away from the two wings of the compliant body to prevent the base portion of the compliant body from being withdrawn through the gap in the absence of sufficient force to deform the base portion of the compliant body that would enable the base portion of the compliant body to pass through the gap.

A cassette according to the present invention may further have another tray, with the tray including one part of the coupling mechanism, and the another tray including another part of the coupling mechanism. The one part of the coupling mechanism may have first and second latch bars, and the another part of the coupling mechanism may have first and second catch bars each configured to disengageably engage one of the latch bars in the coupled state.

Each catch bar may be rotatably coupled to the another tray with a respective hinge.

A tie bar may connect the catch bars.

The coupling mechanism may further have a knob connected to one of the latch bars, and another knob connected to another one of the latch bars to enable the movement of the latch bars toward and away from one another.

The coupling mechanism may further include first and second receptacles. In the coupled state, the first latch bar engages the first catch bar in the first receptacle, and, in the coupled state, the second latch bar engages the second catch bar in the second receptacle. The first and second catch bars may be withdrawn from the first and second receptacles when the first and second latch bars disengage from the first and second catch bars.

A resilient body may be provided to connect the first latch bar to the second latch bar. The resilient body is arranged so that the displacement of the latch bars toward one another by manual movement of the bars compresses the resilient body.

Other features and advantages of the present invention will become apparent from the following description of the invention which refers to the accompanying drawings.

DETAILED DESCRIPTION OF EMBODIMENTS OF THE INVENTION

Figure 1:
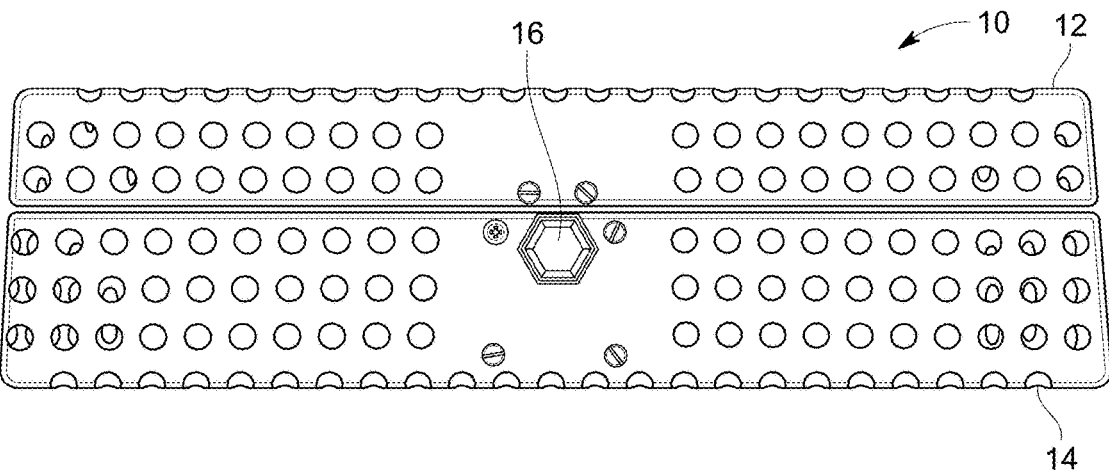
FIG. 1 shows a front view of a cassette according to the present invention, in the closed, locked state.

Referring to FIG. 1, a cassette 10 according to the present invention includes a first (top) tray 12, and a second (bottom) tray 14. A locking mechanism (described below) is provided to lock the first tray 12 and the second tray 14 to one another and keep the first tray 12 and the second tray 14 in a closed, locked state. The locking mechanism includes a push button 16, which when pressed inwardly toward the interior of the cassette 10 releases a lock catch 46 that is secured by the locking mechanism permitting the first tray 12 to be rotated relative to the second tray 14 thereby permitting the opening of the cassette 10. The lock catch 46 may be a flat body made of a metal with an opening defined therein as described below.

Figure 2:
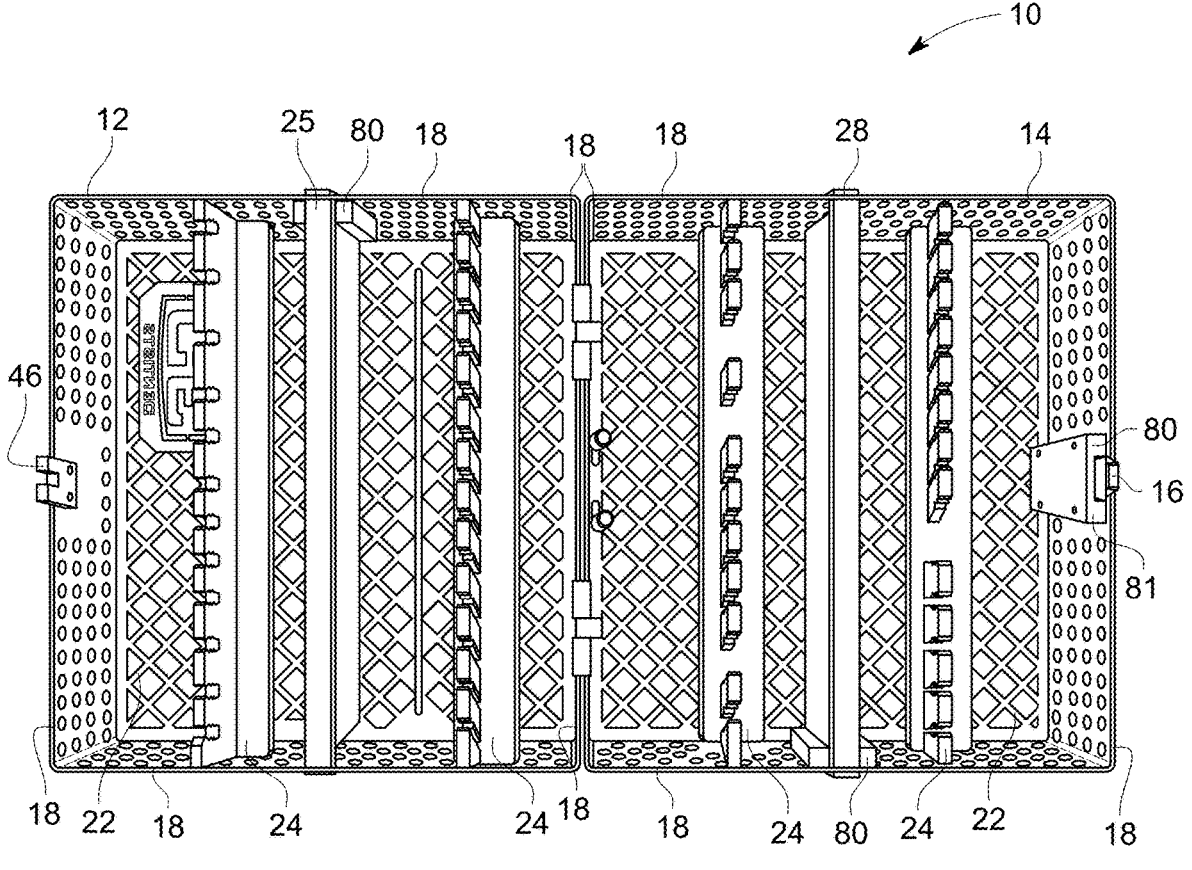
FIG. 2 shows the cassette of FIG. 1 in the open state.
Figure 3A:
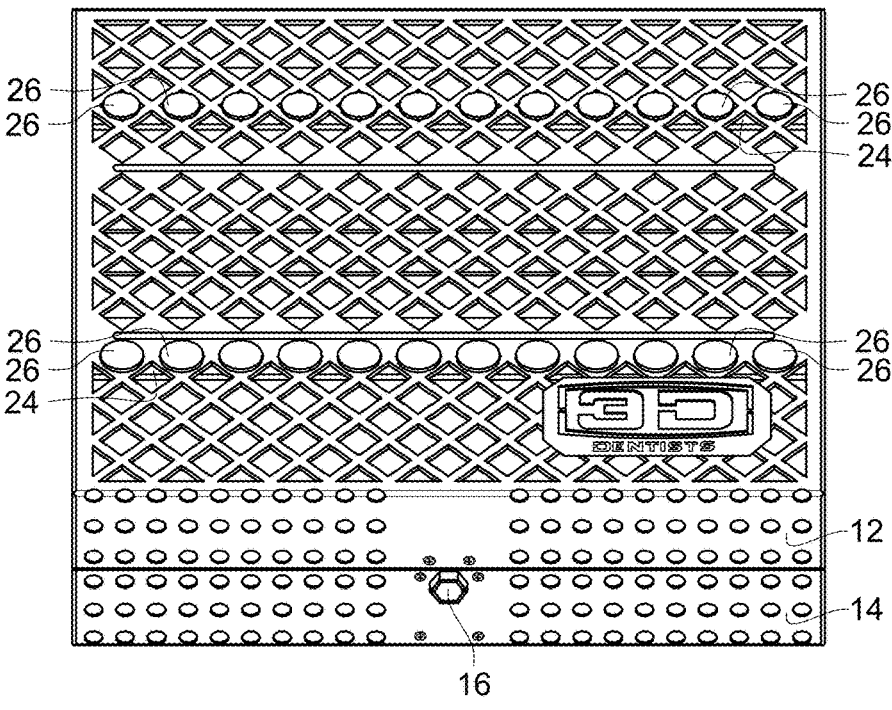
FIG. 3A shows a top, front, perspective view of the cassette of FIG. 1 in the closed, locked state, showing a push button of a locking mechanism associated with the bottom tray of the cassette.
Figure 3B:
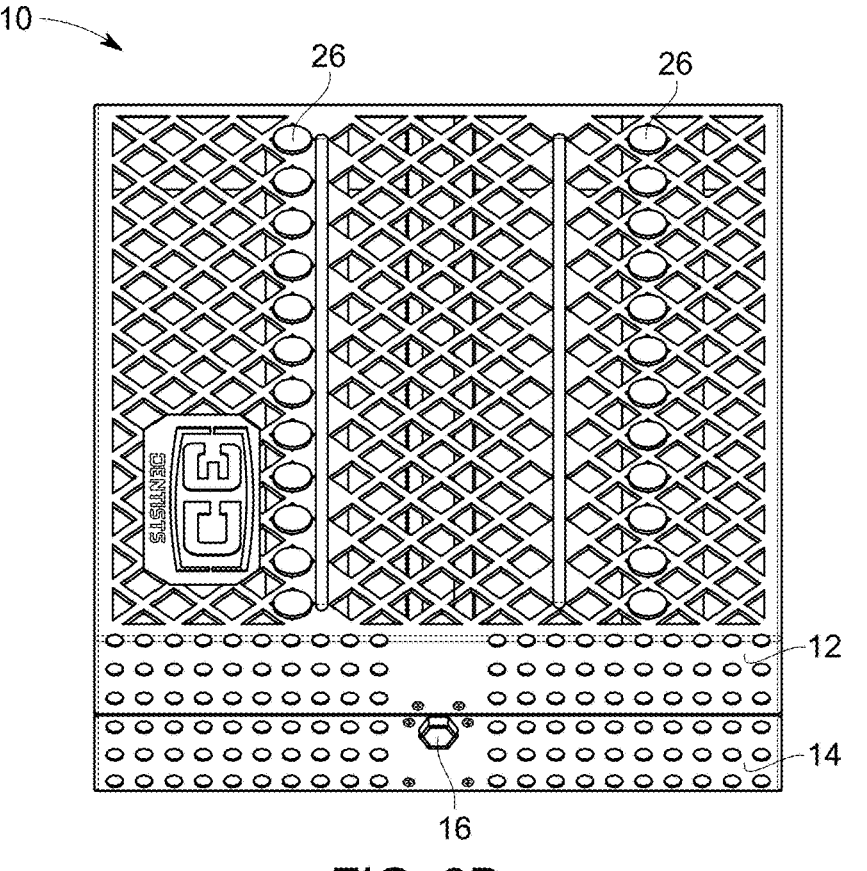
FIG. 3B shows a top, left side, perspective view thereof, showing a push button of a locking mechanism associated with the top tray of the cassette.
Figure 3C:
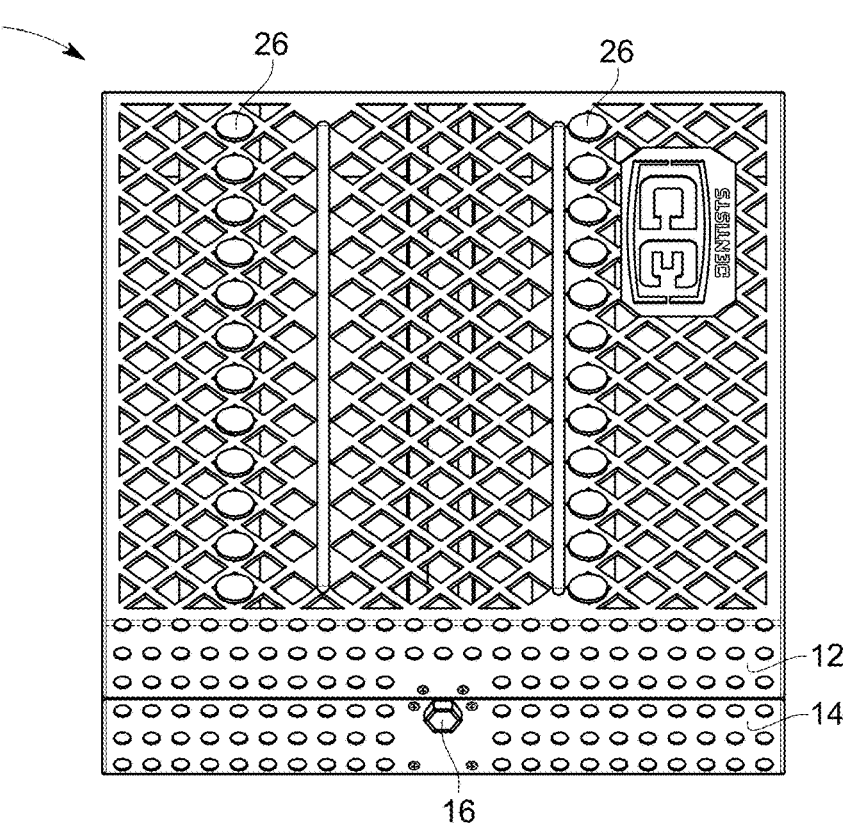
FIG. 3C shows a top, right side, perspective view thereof, showing a push button of a locking mechanism associated with the bottom tray of the cassette.
Figure 3D:
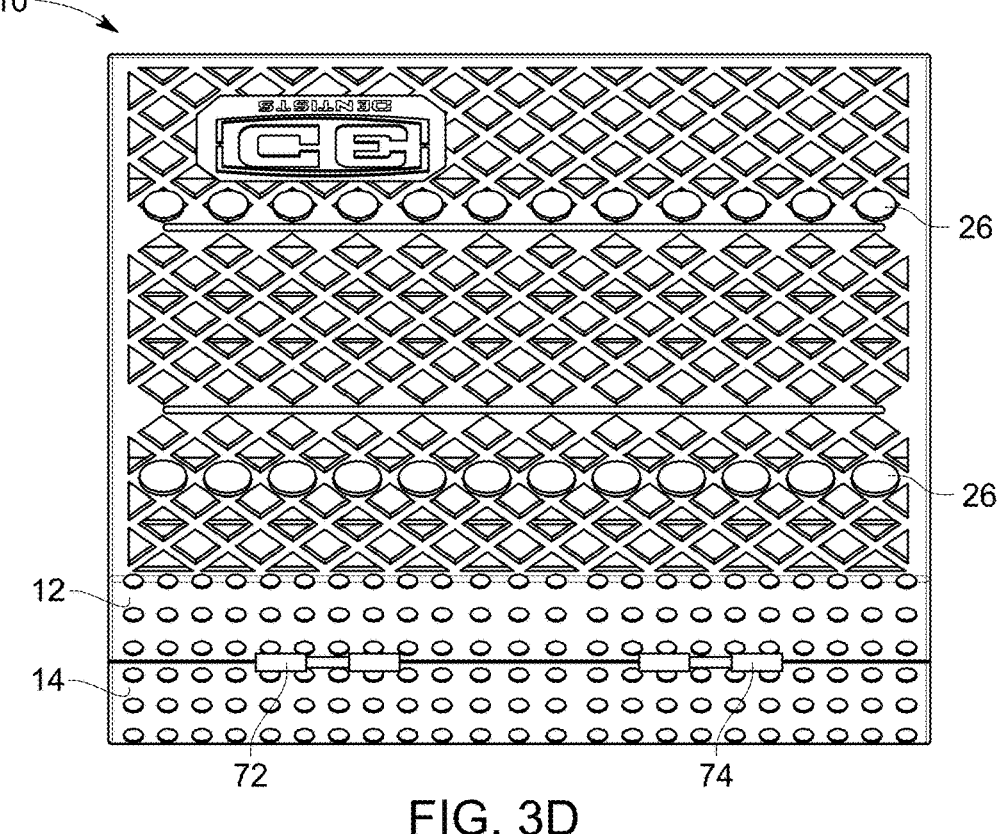
FIG. 3D shows a top, rear view of the cassette of FIG. 1.

Referring to FIG. 2, which shows the cassette 10 in an open, unlocked state, each tray 12, 14 includes a plurality (for example, four) sidewalls 18, extending from a respective edge of a panel 20 to define a reception space 22 in which dental instruments may be received. The walls 18 and the panels 20 have openings therein to permit the entry of steam, for example, into the reception spaces 22 in order to sterilize dental instruments that are housed in the cassette 10.

The cassette 10 may have in each reception space 22 flexible racks 24 made, for example, from silicone, resin or sterilizable plastic material. The flexible racks 24 are provided to secure dental instruments inside of spaces 22 as is well known.

Each rack 24 may have a plurality of flexible anchors 26 (see for example FIGS. 3A-3D) each retractably insertable in (for example, snapped in) a respective opening of a respective web 20, whereby each rack 24 may be removably coupled to a respective panel 20.

Figure 4A:
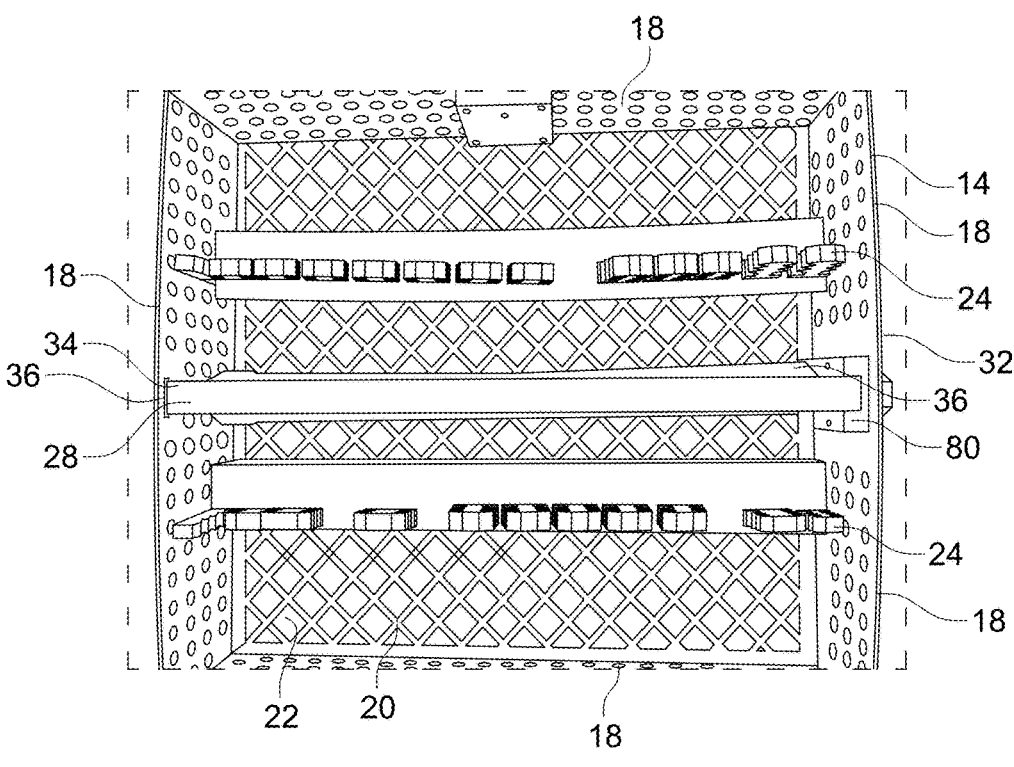
FIG. 4A shows a lock bar of a cassette according to the present invention installed in the bottom tray thereof.
Figure 4B:
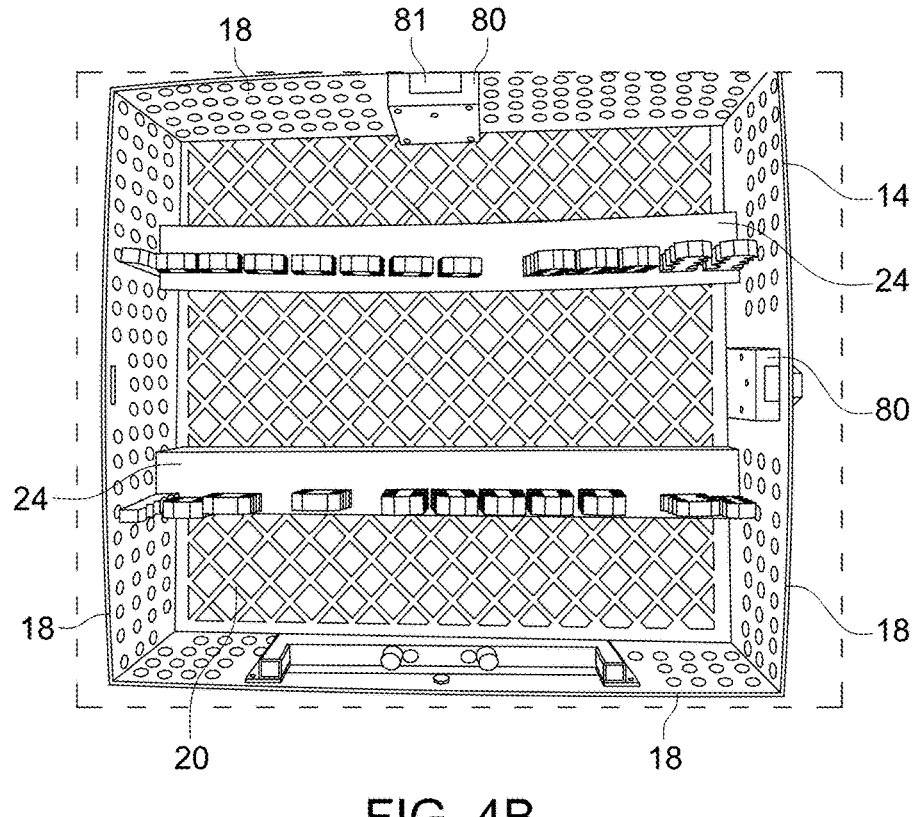
FIG. 4B shows the bottom tray of the cassette of the present invention with the lock bar removed.

As seen in FIG. 2, each tray 12, 14 includes a pair of racks 24 installed therein. A lock bar 28 is provided in each tray 12, 14, with an associated rack 24 on either side thereof. The function of each lock bar 28 is to press the medical or dental instruments received by its associated racks 24 when in a locked state (FIG. 4A). Once a lock bar 28 is unlocked and removed (FIG. 4B), the medical or dental instruments may be removed from the lock bar's associated racks 24.

Each lock bar 28 may be a rigid body made, for example, from a metal that is capable of withstanding sterilization. One end 32 of each lock bar 28 may have a lock catch 46 that is locked to a wall 18 using the same locking mechanism, for example, as the locking mechanism that permits the locking of one tray 12 to the other tray 14. The other end 34 of each lock bar 28 may have a tongue 36 (FIG. 4C), which is received in a slot 38 defined in a wall 18 opposite the one end 32 when the one end 32 is in a locked state (FIG. 4A).

Figure 4C:
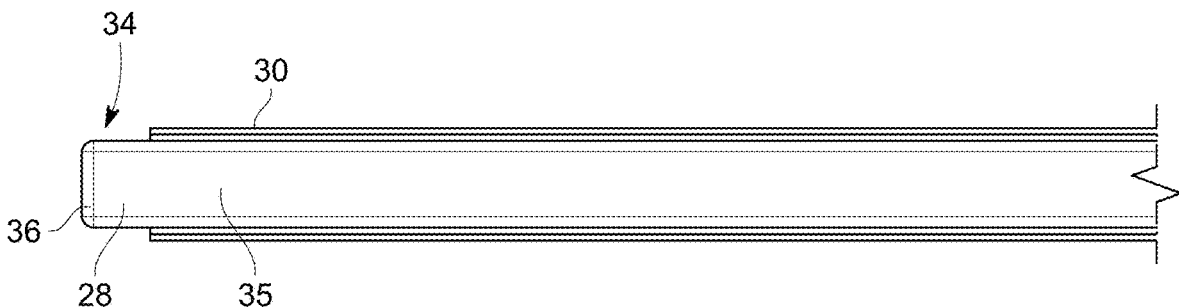
FIG. 4C shows a portion of the lock bar of the cassette of the present invention having a tongue that is receivable in a slot defined in a wall of a tray.
Figure 4D:
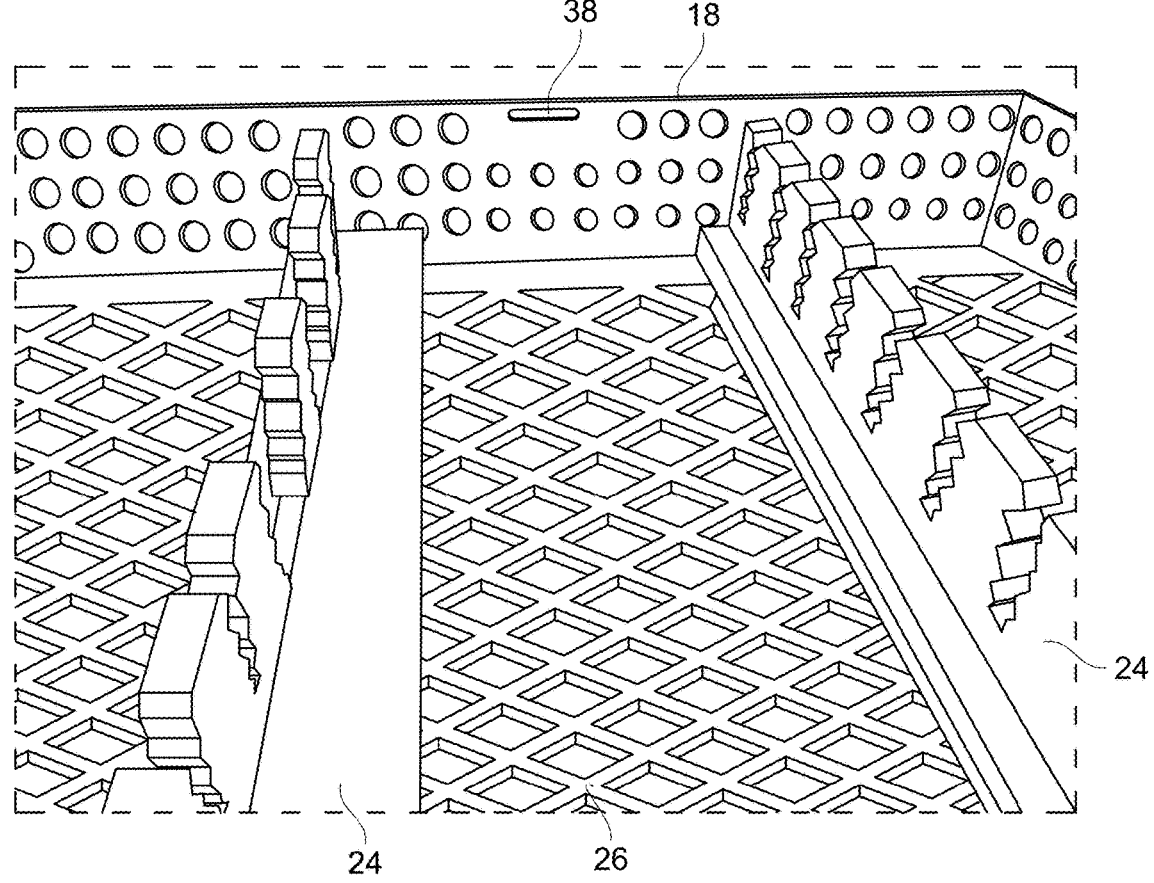
FIG. 4D shows a slot defined in a wall of a tray to receive the tongue portion of a lock bar of a cassette according to the present invention.
Figure 4E:
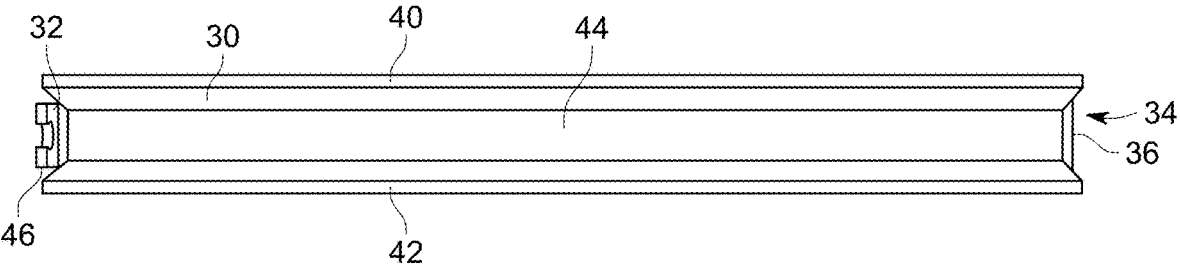
FIG. 4E shows a lock bar of a cassette according to the present invention with a lock catch at one end that is lockable by a locking mechanism of a cassette according to the present invention, and a tongue at another end that is received in a slot defined in a wall of a tray of a cassette according to the present invention.
Figure 4F:
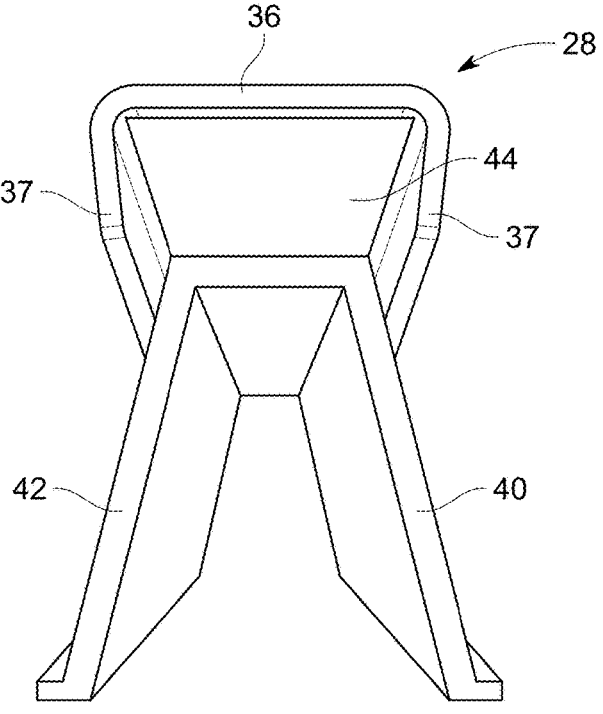
FIG. 4F shows a compliant body integrated with a lock bar of a cassette according to the present invention.

Referring to FIGS. 4C, 4D, and 4E, each lock bar 28 may include a compliant body 30 extending preferably between the one end 32 to the other end 34. Each compliant body 30 is made of a flexible and compliant material such as silicone, resin or sterilizable plastic material. Each compliant body 30 includes a first wing 40, and a second wing 42, each extending from a base portion 44 that is attached to the lock bar 28.

The base portion 44 of the compliant body may be detachably attached and re-attachable to the lock bar 28. For example, the lock bar 28 may have a base 35 (FIG. 4C), and two wing portions 37 extending from the base 35 to form a C-shaped channel. The wing portions 37 are bent to tilt inwardly toward one another. The base portion 44 of the compliant body 30 may have a cross-section normal to its length that becomes larger in the direction away from the wings 40,42. The narrowest part of the base portion 44 is preferably about the same dimension as the gap between the free edges of the wing portions 37 of the lock bar 28, whereby the base portion 44 becomes trapped in the C-shape channel of the lock bar 28 when received in the C-shaped channel of the lock bar 28, and can be removed either by sliding the base portion 44 out of an open end of the C-shaped channel or by pulling the compliant body 30 away from the C-shaped channel of the lock bar 28 with enough force to deform the base portion 44 so that it may pass through the gap between the wing portions 37 of the lock bar 28.

When the compliant body 30 is pressed toward the medical or dental instruments received in the pair of racks 24 associated with the lock bar 28, the wings 40, 42 spread over the medical or dental instruments, whereby the compliant body 30 avoids damage to the medical or dental instruments that could be caused by direct contact with the lock bar 28, which is a rigid body. Furthermore, the spreading of the wings 40,42 of each compliant body 30 allows for a more intimate contact as the wings 40,42 adjust to the shape of the dental instruments.

Figure 5A:
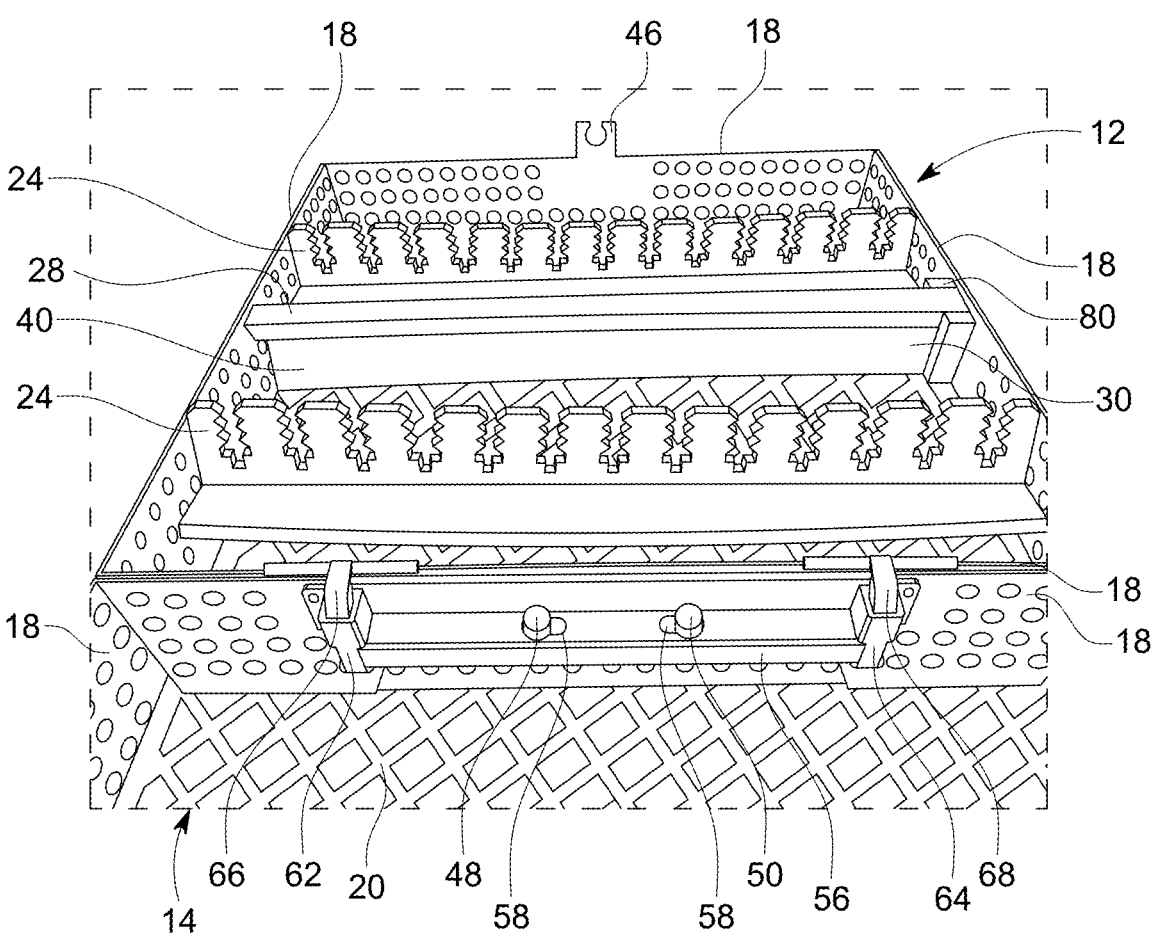
FIG. 5A shows a coupling mechanism in a coupled state coupling the top tray and the bottom tray of the cassette according to the present invention.

Trays 12, 14 are detachably attachable to one another by a coupling mechanism that also enables the rotation of one tray 12 relative to the other tray 14, when the trays are coupled to one another as seen in FIG. 2 and also FIG. 5A.

Figure 5B:
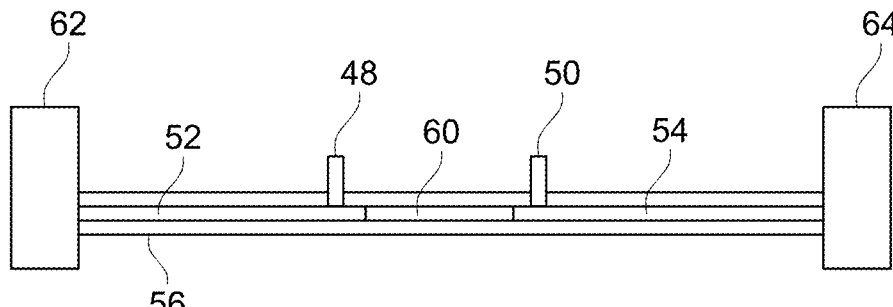
FIG. 5B schematically illustrates a first part of the coupling mechanism with the latch bars thereof retracted into a housing.
Figure 5C:
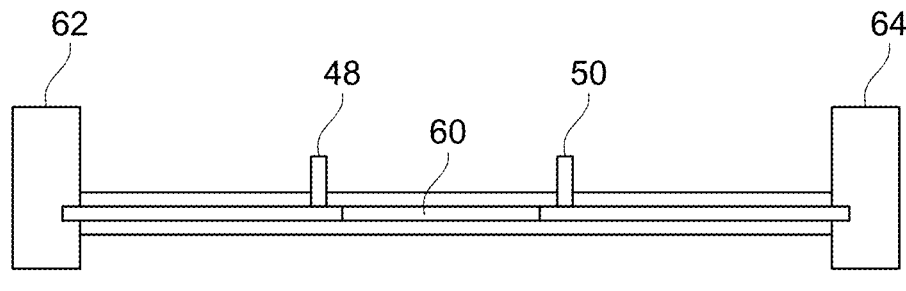
FIG. 5C schematically illustrates the first part of the coupling mechanism with the latch bars thereof extending into respective receptacles.
Figure 5D:
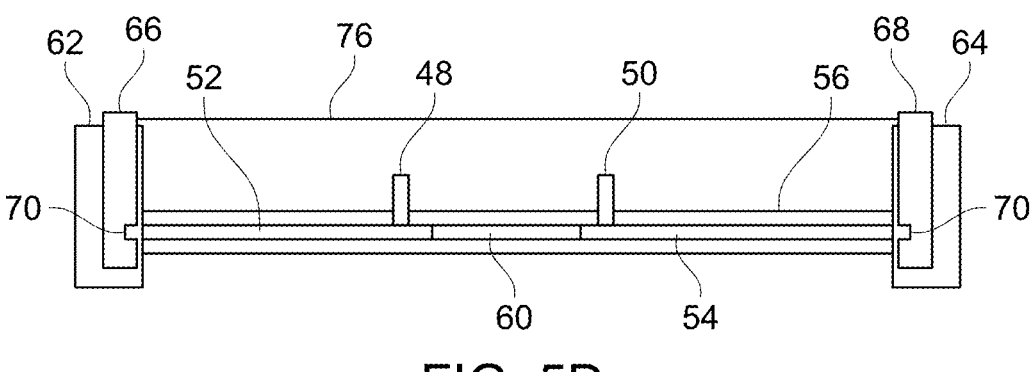
FIG. 5D schematically illustrates the first part of the coupling mechanism with the latch bars thereof retracted into the housing, and the second part of the coupling mechanism having catch bars received in respective receptacles, the first and the second parts being in an uncoupled state.
Figure 5E:
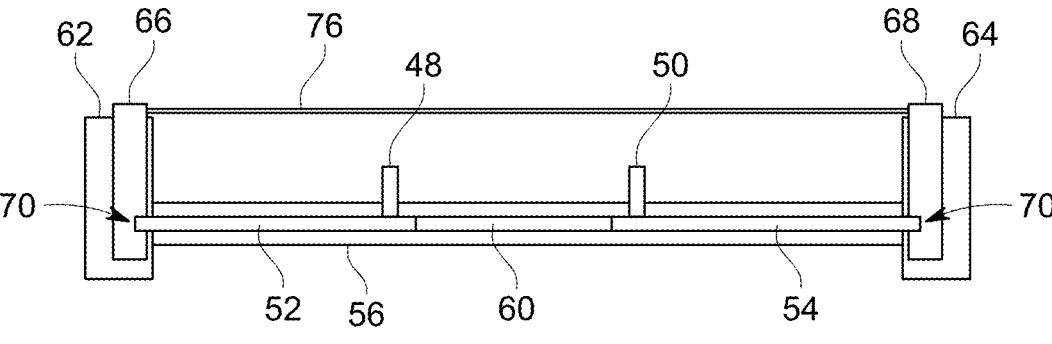
FIG. 5E schematically illustrates the first part of the coupling mechanism with the latch bars thereof extending into the receptacles and engaging the catch bars of the second part thereof to couple the first part and the second part of the coupling mechanism.
Figure 5F:
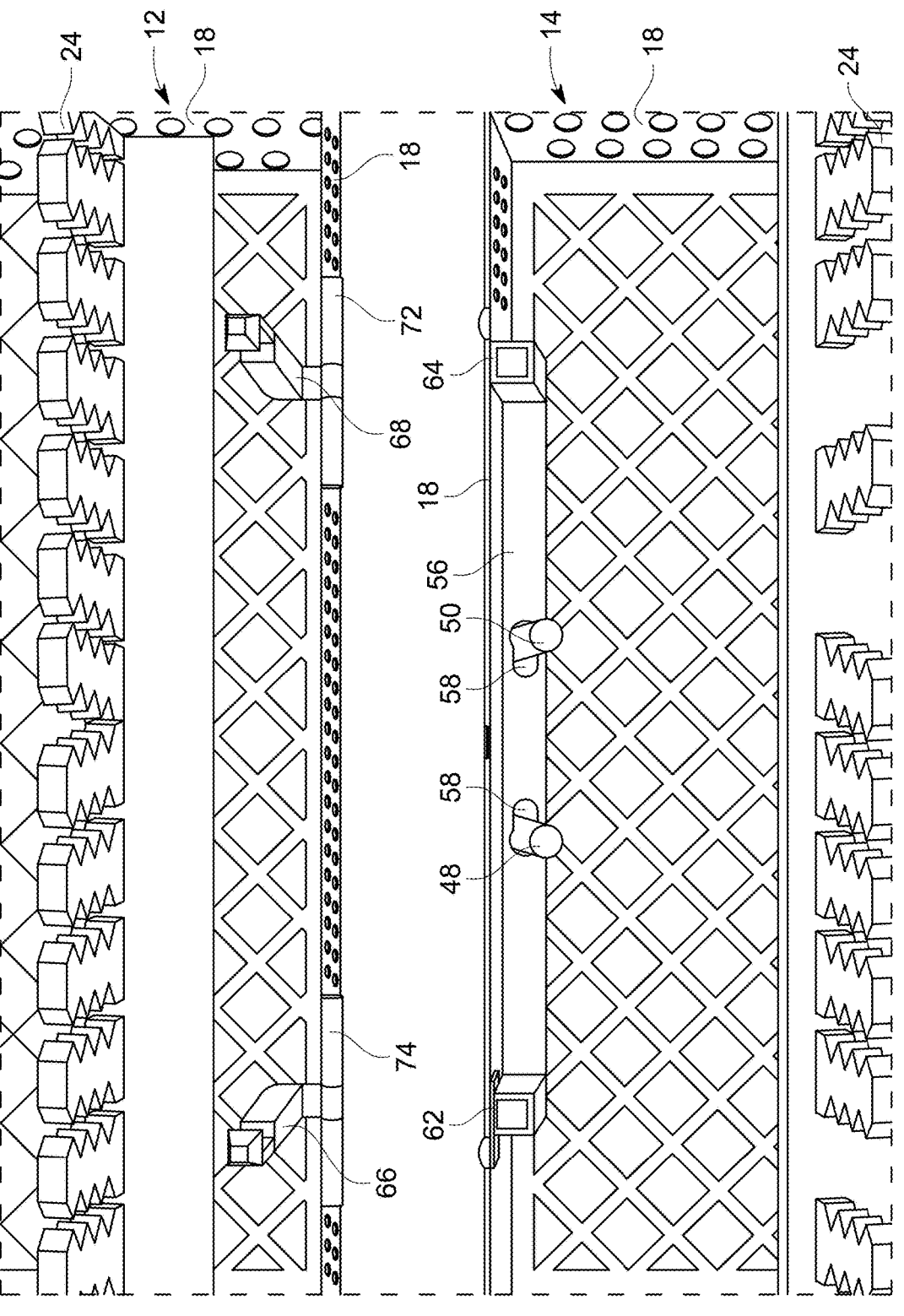
FIG. 5F shows a top view of the first part and the second part of the coupling mechanism in the uncoupled state.
Figure 5G:
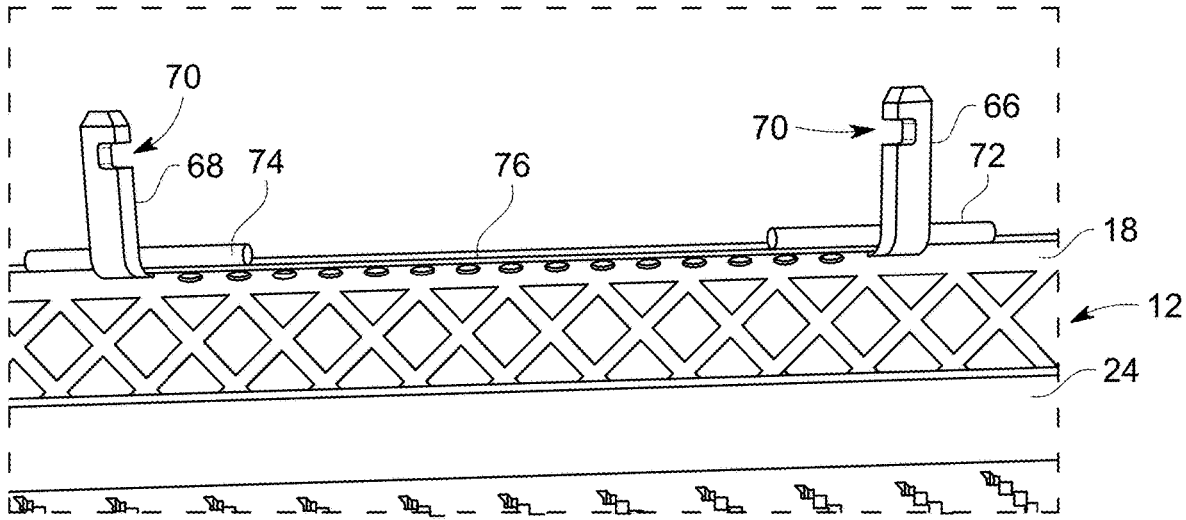
FIG. 5G shows a top view of the second part of the coupling mechanism in the uncoupled state.

Referring to FIGS. 5A-5G, a first knob 48 and a second knob 50 are provided to permit manual operation of the coupling mechanism. The first knob 48 is attached to a first latch bar 52. The second knob 50 is attached to a second latch bar 54. Latch bars 52 and 54 reside in a housing 56 and are arranged to move relative to (for example slide inside) the housing 56. The housing 56 may be for example a tube in which the latch bars 52,54 are arranged to slide. The housing 56 is fixed (for example, with screws or the like) to the rear wall 18 of, for example, the second tray 14 at a location opposite the front wall 18 on which a locking mechanism associated with a push button 16 is located, as shown in FIG. 2. Knobs 48, 50 extend through slots 58 defined in the housing 56. The slots 58 are dimensioned to permit the knobs 48, 50 to move toward and away from each other relative to the housing 56. A spring 60 or the like resilient body is provided between the latch bars 52,54 to push the latch bars 52,54 away from one another when no force is applied to knobs 48, 50. In this state, the free end of the latch bar 52 extends into a first receptacle 62 located at one end of the housing 56, and the free end of the second latch bar 54 extends into a second receptacle 64 located at the opposite end of the housing 56. When knobs 48,50 are pushed towards one another and moved in slots 58, the free ends of latch bars 52,54 are retracted from the receptacles 62,64 toward the housing 56. In this state, a first catch bar 66 and a second catch bar 68 are disengaged from latch bars 52,54, are released, and may be withdrawn from the first receptacle 62, and the second receptacle 64, whereby the first tray 12 and the second tray 14 may be detached from one another as illustrated in FIG. 5B.

Each catch bar 66, 68 has a notch 70 defined therein to face and receive a free end of a respective bar 52,54 when catch bars 66,68 are inserted in the receptacles 62,64, whereby the catch bars 66,68 may not be retracted from the receptacles 62,64, unless the free ends of the bars are retracted from the receptacles 62,64 (as described above) far enough away from the notches 70 to permit removal of the catch bars 66,68.

The proximal end of the first catch bar 66 is rotatably fixed (with a first hinge 72, for example) to a wall 18 of the first tray 12, while the proximal end of the second catch bar 68 is rotatably fixed (with a second hinge 74, for example) to the same wall 18 of the first tray 12 spaced from the first catch bar 66. In order to enable the rotation of the catch bars 66,68 together, the catch bars 66,68 are fixed to one another with a tie bar 76, which is an elongated body having one end attached to the first catch bar 66 at a location closer to the proximal end of the first catch bar 66 than the distal (free) end thereof. Similarly, the other end of the elongated body of the tie bar 76 is attached to the second catch bar 68 at a location closer to the proximal end of the second catch bar 68 than the distal (free) end thereof. The proximal ends are closer to hinges 72,74 than the distal ends.

Referring to FIGS. 6A-6G, the locking mechanism for locking the trays 12,14, or locking a lock bars 28, includes a lock pin 78. The lock pin 78 has one end connected to a push button 16, and another end connected to a spring 82 or some other resilient body. The end of the lock pin 78 that is connected to a push button 16 extends through a wall 18 of a tray 12 or 14. The other end of the lock pin 78 resides in a lock housing 80, which is arranged in the reception space 22 of the second tray 12 or 14. The lock housing 80 houses the spring 82. The spring 82 urges the lock pin 78 away from the housing 80 when no force is applied to the push button 16. In this state, the lock pin 78 can lock a lock catch 46 that is fixed to a wall 18 of a tray 12 or 14, or at an end of a lock bar 28. When sufficient force is applied to the push button 16 to push the lock pin 78 toward the housing 80, the lock catch 46 is unlocked. A locking mechanism may be integrated with a tray 12 or 14 using screws or the like to attach the housing 80 of the locking mechanism to the interior surface of one of the walls 18 of the tray 12 or 14.

Referring back to FIGS. 2 and 3A-3D, a locking mechanism may be arranged in the second tray 14 at the front wall 18 of the second tray, while the front wall of the first tray 12 may be provided with a lock catch 46. In addition, a locking mechanism may be provided at the left side wall of the first tray 12 with a slot 38 provided at the right side wall 18 of the first tray 12. Furthermore, a locking mechanism may be provided at the right side wall of the second tray 14 with a slot 38 provided in the left side wall 18 of the second tray 14.

Specifically, lock pin 78 has a first section 84 and a second section 86. The first section 84 has a diameter that is smaller than the diameter of the second section 86. As seen, in FIG. 6C, the lock catch 46 is a body that includes a cutout 88. The cutout 88 has a first section 90 that is wider than the first section 84 of the lock pin 78 but less wide than the second section 86 of the lock pin 78. In addition, the cutout 88 has a second section 92 that is wide enough to receive the second section 86 of the lock pin 78. Consequently, when no force is applied to the push button 16, and the second section 86 of the lock pin 78 is received in the second section 92 of the cutout 88, the lock catch 46 is coupled to the lock pin 78 and locked. To unlock the lock catch 46, the push button 16 must be pressed hard enough so that the first section 84 of the lock pin 78 is aligned with the first section 90 of the cutout 88, thereby allowing the lock catch 46 to be withdrawn.

Figure 6A:
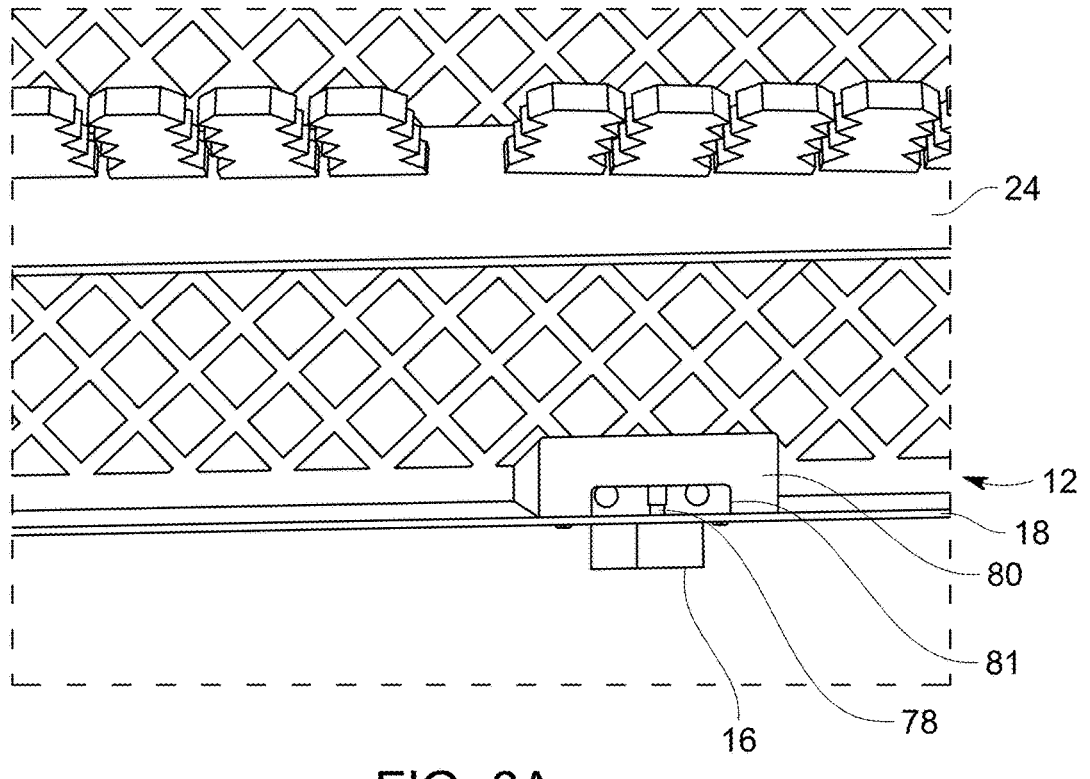
FIG. 6A shows a top view of a locking mechanism of a cassette according to the present invention.
Figure 6B:
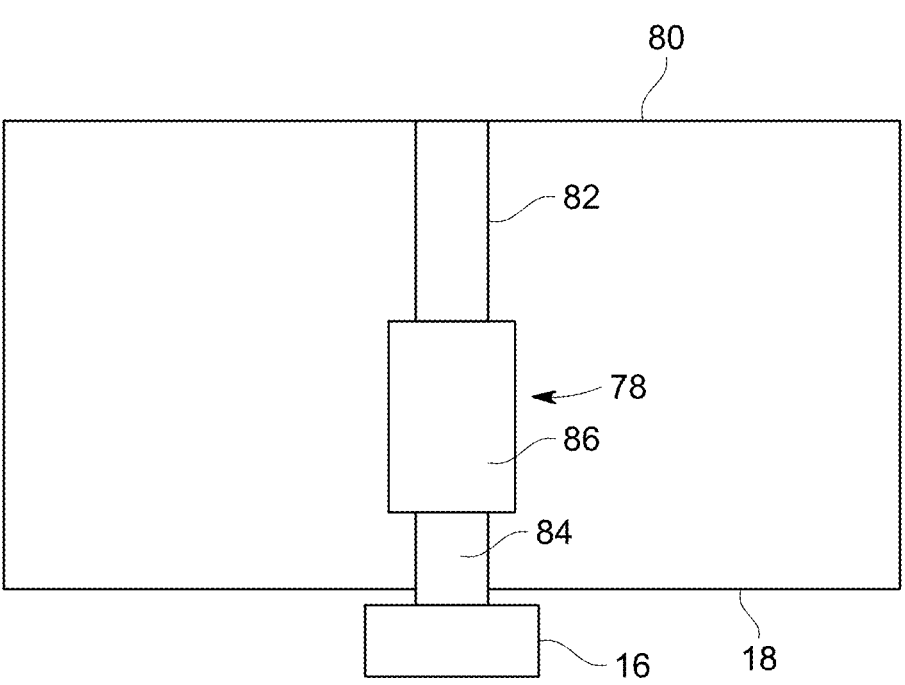
FIG. 6B is a schematic illustration of a locking mechanism of a cassette according to the present invention.
Figure 6C:
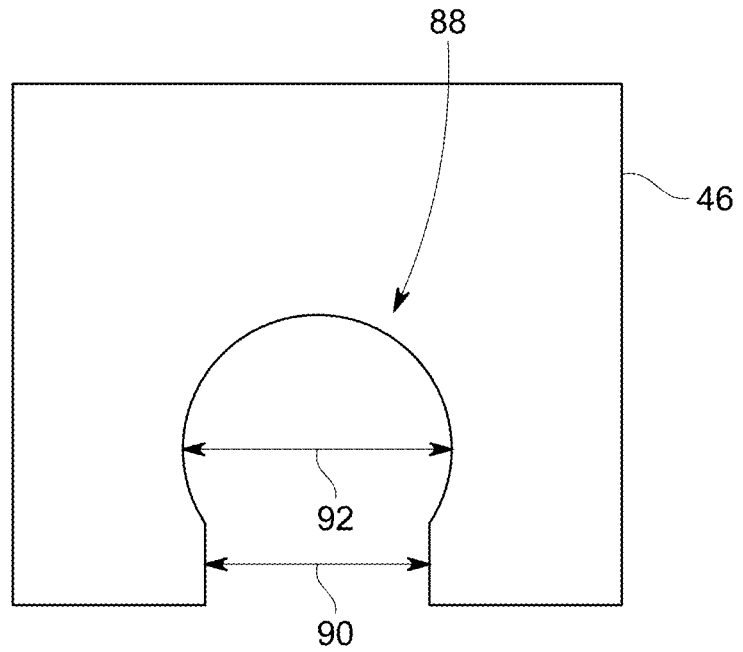
FIG. 6C schematically illustrates a lock catch that can couple to a locking mechanism of a cassette according to the present invention.
Figure 6D:
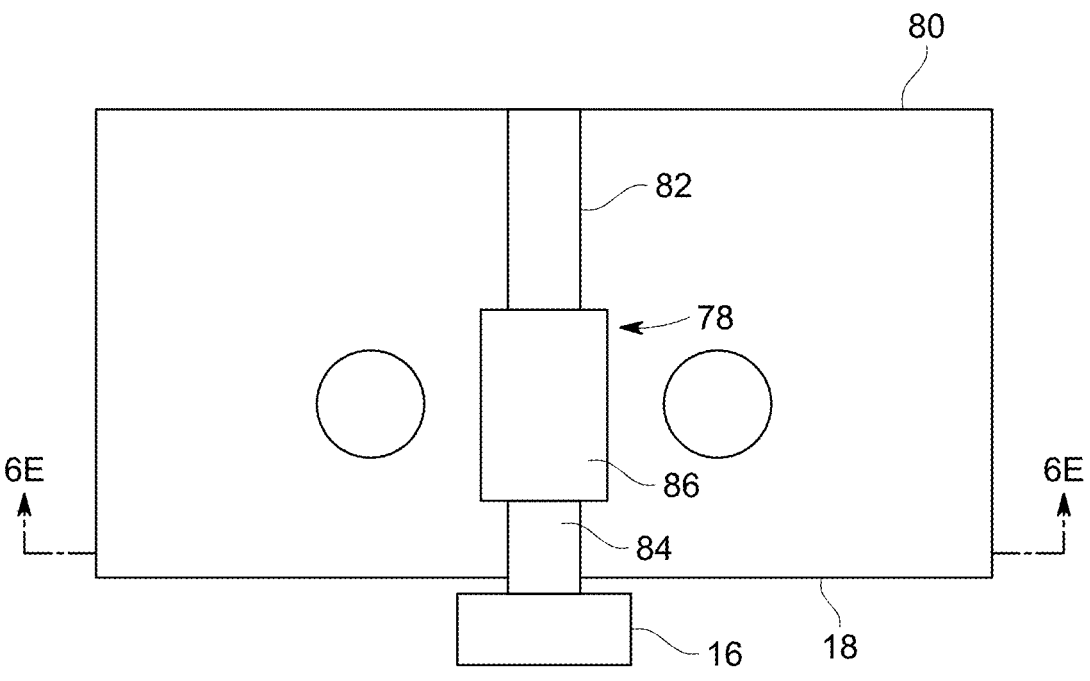
FIG. 6D is a schematic illustration of a second variation of a locking mechanism of a cassette according to the present invention.
Figure 6E:
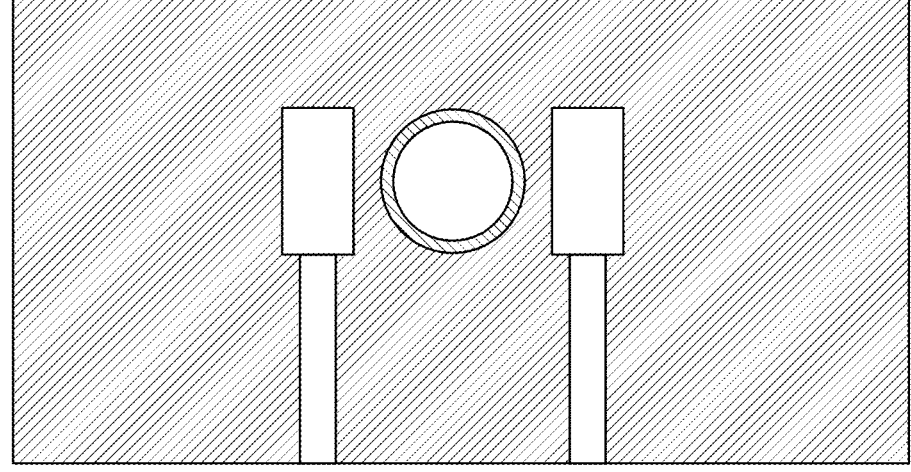
FIG. 6E is a schematic illustration of the second variation along line 6E-6E in FIG. 6C, viewed in the direction of the arrows.
Figure 6F:
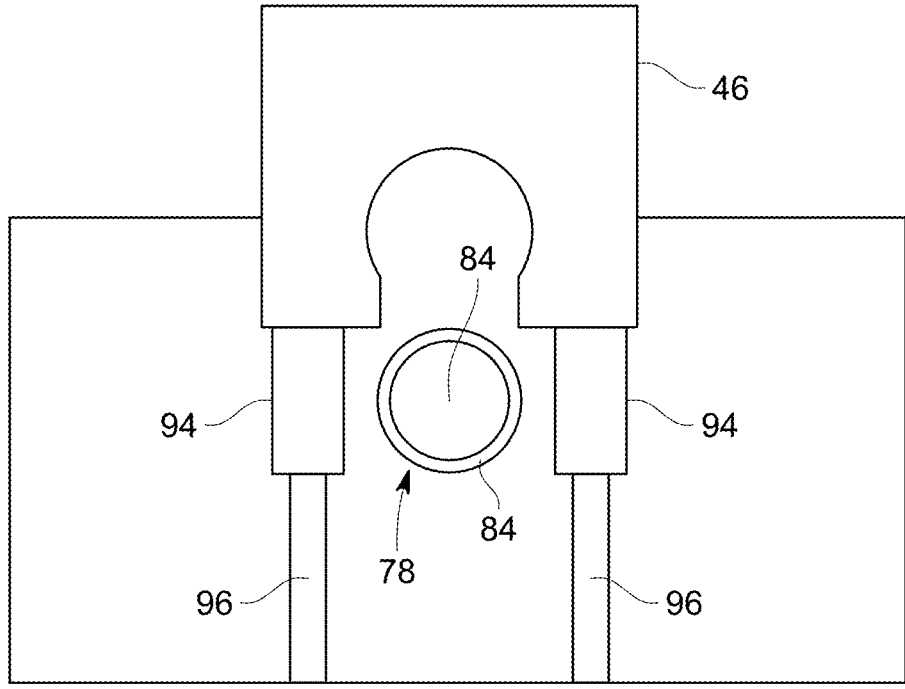
FIG. 6F illustrates the lock catch and the locking mechanism in a disengaged state.
Figure 6G:
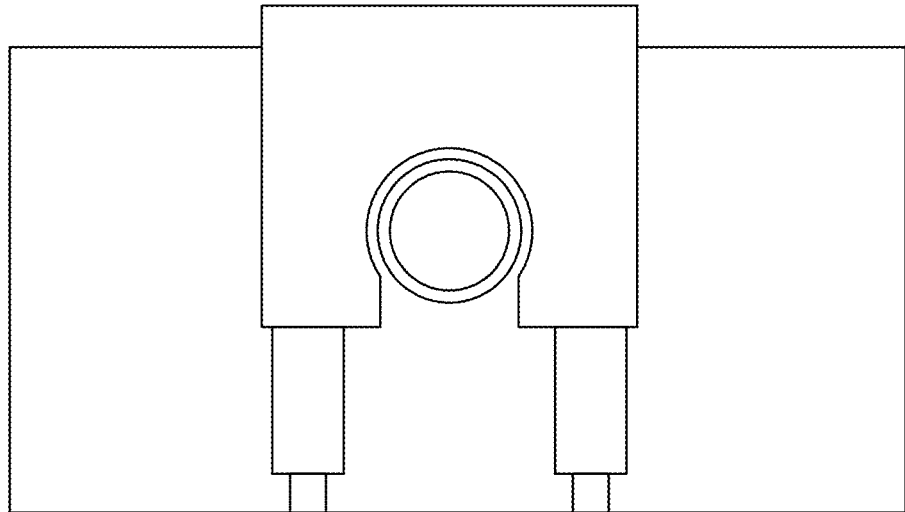
FIG. 6G illustrates the lock catch and the locking mechanism in an engaged (locked) state.

Referring to FIGS. 6F and 6G, as the first section 84 of the lock pin 78 is being inserted in the first section 90 of the cutout 88 of a lock catch 46, surfaces of the lock catch 46 adjacent the first section 90 of the cutout 88 engage the second section 86 of the lock pin 78 and push the lock pin 78 toward the interior of the lock housing 80 as the surfaces adjacent the first section 90 of the cutout 88 slide against the second section 86 of the lock pin 78. Once the surfaces adjacent the first section 90 of the cutout 78 no longer engage the second section 86 of the lock pin 78, the second section 86 of the lock pin 78 is urged into the second section 92 (FIG. 6G) of the cutout 88 by the spring 82, whereby the lock catch 46 is locked in the second section 92.

Referring to FIGS. 6D, 6E, 6F, and 6G, the locking mechanism may further include two push pins 94, the purpose of which is to push away the lock catch 46 when the lock catch 46 is released from the lock pin 78. Each push pin 94 used in this variation may be connected to and urged by a spring 96 or the like resilient body, which is arranged to push against the interior surface of the lock housing 80. For example, each spring 96 may be sandwiched between a push pin 94 and the interior surface of the lock housing 80. When a lock catch 46 is received in the lock housing 80 through an access opening 81 (see FIG. 6A), it abuts the free ends of the push pins 94 and as is pushed further into the lock housing 80 the springs 96 are compressed. As the first section of the lock pin 78 is being inserted into the first section 90 of the cutout 88 of the lock catch 46, surfaces of the lock catch 46 adjacent the first section 90 of the cutout 88 engage the second section 86 of the lock pin 78 and push the lock pin 78 toward the interior of the lock housing 80, while the surfaces adjacent the first section 90 of the cutout 88 slide against the second section 86 of the lock pin 78. Once the surfaces adjacent the first section 90 of the cutout 78 no longer engage the second section 86 of the lock pin 78, the second section 86 of the lock pin is urged into the second section 92 of the cutout 88 by the spring 82, whereby the lock catch 46 is locked in. In this state, the springs 96 of the push pins 94 are compressed (loaded). Once the lock catch 46 is released (unlocked) from the lock pin 78 by pushing in the push button 16, the push pins 94 are urged in a direction away from the interior of the lock housing 80 as the springs 96 are decompressed (unloaded), thereby pushing the lock catch 46 away from the lock housing 80. Consequently, if the locking mechanism with the spring-loaded push pins 94 is used to lock the trays 12,14, the unlocking of the lock catch 46 would pop open the two trays 12,14. It should be noted that it is possible to use one spring-loaded push pin 94, although using two push pins is preferred in that it allows for using smaller springs.

The trays 12, 14 and the lock bar 28 may be made of stainless steel or aluminum alloys suitable for sterilization.

While FIGS. 6F and 6G show a locking mechanism with push pins 94, it should be noted that the locking and the unlocking operation of a locking mechanism without push pins 94 (FIG. 6B) is the same and thus not illustrated.

In the embodiment disclosed herein, the locking mechanism for locking the lock catch 46 of a lock bar 28 is the type as shown in FIG. 6B (without a push pin 94), while the locking mechanism used to lock trays 12, 14 is of the type that includes push pins 94. It should be noted, however, that, in other embodiments, the push pins 94 may be omitted from all of the locking mechanisms, or a push pin 94 may be provided for one or all of the locking mechanisms of the lock bars 28, with or without push pins 94 for a locking mechanism that locks the two trays.

Furthermore, while in the disclosed embodiment, a locking mechanism for locking the trays 12,14 is integrated with the second (bottom) tray 14, in another embodiment, the locking mechanism for locking the trays 12,14 could be integrated with the first (top) tray 12 to couple to a lock catch 46 that is integrated with the second (bottom) tray 14.

In addition, while, in the embodiment shown, the first part of the coupling mechanism is integrated with the second (bottom) tray 14, the first part could be integrated with the first (top) tray 12, and the second part integrated with the second (bottom) tray 14.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A dental cassette, comprising:
   a tray that comprises a plurality of walls extending from a panel to define a reception space for receiving at least one dental instrument;
   another tray;
   a locking mechanism that includes a lock pin, and a resilient body coupled to the lock pin to urge the lock pin toward a lock position, wherein the lock pin is configured to lock a lock catch, wherein the lock catch is attached to the another tray, wherein the lock pin has a first section and a second section, the first section of the lock pin having a diameter smaller than the second section of the lock pin, wherein the lock catch is a body having a cutout that has a first section that is wider than the first section of the lock pin but narrower than the second section of the lock pin, wherein the cutout has a second section that is wide enough to receive the second section of the lock pin, and wherein, in a locked state, the second section of the lock pin is in the second section of the cutout, and in a released state, the second section is outside the second section of the cutout to permit the first section of the lock pin to pass through the first section of the cutout;
   at least one push pin that abuts the lock catch, the push pin is connected to another resilient body that is compressed by the push pin in the locked state, whereby the lock catch is pushed away by the push pin in the released state as the another resilient body decompresses; and
   a push button connected to the lock pin, wherein applying a force sufficient to compress the resilient body moves the lock pin from the locked state to the released state.

2. The dental cassette of claim 1, wherein the locking mechanism includes a lock housing.

3. The dental cassette of claim 1, wherein the cutout is configured so that surfaces adjacent the first section of the cutout engage the second section of the lock pin as the first section of the lock pin is inserted into the first section of the cutout to compress the resilient body, and wherein when the surfaces adjacent the first section of the cutout no longer engage the second section of the lock pin, the compressed resilient body decompresses and urges the second section of the lock pin to enter the second section of the cutout thereby coupling the lock pin and the lock catch to realize the locked state.

4. The dental cassette of claim 1, wherein the another tray is rotatably coupled to the tray, and wherein the locking mechanism resides at a front wall of the tray in the reception space, and the lock catch resides at a front wall of the another tray.

5. The dental cassette of claim 1, further comprising a lock bar, wherein the lock bar comprises an elongated body having a lock catch at one end thereof, and a tongue at another end thereof, wherein the tongue is receivable in a slot defined in one wall of the tray, and the lock catch is lockable by another locking mechanism located in the reception space and at another wall of the tray opposite the one wall.

6. The dental cassette of claim 5, further comprising a compliant body coupled to the lock bar.

7. The dental cassette of claim 6, wherein the compliant body comprises a base portion, and two wings extending from the base portion.

8. The dental cassette of claim 7, wherein the lock bar includes a base and two wing portions extending from the base of the lock bar to define a channel, wherein the base portion of the compliant body is received in the channel.

9. The dental cassette of claim 8, wherein the wing portions of the lock bar are tilted toward one another, wherein part of the base portion of the compliant body is located in a gap between free edges of the wing portions of the lock bar, and wherein the base portion of the compliant body has a cross-section that widens in a direction away from the two wings of the compliant body to prevent the base portion of the compliant body from being withdrawn through the gap in the absence of sufficient force to deform the base portion of the compliant body that would enable the base portion of the compliant body to pass through the gap.

10. The dental cassette of claim 1, further comprising a coupling mechanism, wherein the one tray includes one part of the coupling mechanism, and the another tray includes another part of the coupling mechanism, wherein the one part of the coupling mechanism includes first and second latch bars, and the another part of the coupling mechanism includes first and second catch bars each configured to engage one of the latch bars in a coupled state.

11. The dental cassette of claim 10, wherein each catch bar is rotatably coupled to the another tray with a respective hinge.

12. The dental cassette of claim 11, further comprising a tie bar connecting the catch bars.

13. The dental cassette of claim 10, wherein the coupling mechanism further comprises a knob connected to one of the latch bars, and another knob connected to another one of the latch bars to enable movement of the latch bars toward and away from one another.

14. The dental cassette of claim 10, wherein the coupling mechanism further comprises first and second receptacles, wherein, in the coupled state, the first latch bar engages the first catch bar in the first receptacle, and, in the coupled state, the second latch bar engages the second catch bar in the second receptacle, and wherein the first and second catch bars may be withdrawn from the first and second receptacles when the first and second latch bars disengage from the first and second catch bars.

15. The dental cassette of claim 14, wherein the coupling mechanism further comprises a knob connected to one of the latch bars, another knob connected to another one of the latch bars to enable manual movement of the latch bars toward and away from one another, and a resilient body connecting the first latch bar to the second latch bar, wherein the resilient body is arranged so that the displacement of the latch bars toward one another by movement of the bars compresses the resilient body.

* * * * *